United States Patent
Jacquot et al.

(10) Patent No.: US 9,464,027 B2
(45) Date of Patent: *Oct. 11, 2016

(54) PRODUCTION OF DIESTERS FROM DINITRILE COMPOUNDS

(75) Inventors: Roland Jacquot, Francheville (FR); Philippe Leconte, Ribeauvillé (FR)

(73) Assignee: RHODIA OPERATIONS, Aubervilliers (FR)

( * ) Notice: Subject to any disclaimer, the term of this patent is extended or adjusted under 35 U.S.C. 154(b) by 1333 days.

This patent is subject to a terminal disclaimer.

(21) Appl. No.: 12/739,213

(22) PCT Filed: Oct. 21, 2008

(86) PCT No.: PCT/EP2008/064218
§ 371 (c)(1),
(2), (4) Date: Dec. 5, 2011

(87) PCT Pub. No.: WO2009/056477
PCT Pub. Date: May 7, 2009

(65) Prior Publication Data
US 2012/0071686 A1    Mar. 22, 2012

(30) Foreign Application Priority Data
Oct. 31, 2007  (FR) .................................... 07 07666

(51) Int. Cl.
*C07C 69/34* (2006.01)
*C07C 67/20* (2006.01)

(52) U.S. Cl.
CPC .................... *C07C 67/20* (2013.01)

(58) Field of Classification Search
CPC .................................................. C07C 69/34
USPC ....................................... 560/193
See application file for complete search history.

(56) References Cited

U.S. PATENT DOCUMENTS 3,795,693 A * 3/1974 Dorfman et al. ..... C07C 255/19
                                                          554/113
2009/0224204 A1   9/2009 Marion et al.
2009/0326261 A1* 12/2009 Leconte et al. ............... 560/129

FOREIGN PATENT DOCUMENTS

DE         730 518 C       1/1943
WO    WO2007/101929 A      9/2007
WO    WO2008/009792 A      1/2008

OTHER PUBLICATIONS

Bogert et al., Journal of the American Chemical Society, Jan. 1, 1902, vol. 24 pp. 20-25.*
Xue Cuihua et al. "Transformation of Amides Into Esters by the use of Chlorotrimethylsilane" *Journal of the Chinese Chmical Society* Jan. 1, 2004 vol. 51 No. 2 pp. 359-362 XP008077858.
Boger M T "On the Production of the Imides of Succinic and Glutaric Acids by the Partial Hydration of the Corresponding Nitriles" *Journal of the American Chemical Society* Jan. 1, 1902 vol. 24 pp. 20-25 XP002484940.
Laeckmann D. et al. "Synthesis and Biological Evaluation of Aroylguanidines Related to Amiloride as Inhibitors of the Human Platelet Na<+>/H<+> Exchanger" *Bioorganic & Medicinal Chemistry* Jan. 1, 2002 vol. 10 No. 6 pp. 1793-1804 XP002429666.
Bizilj S "The Self-Reactions of 1-(Methoxycarbonyl)-1-Methylethyl and higher Ester Radical: Combination vs. Disproportionation and Oligomeric Products from Secondary Reactions" *Australian Journal of Chemistry* 1985 vol. 38 No. 11 pp. 1657-1673 XP008093241.
International Search Report—PCT/EP2008/064218 dated Jan. 28, 2009.

* cited by examiner

*Primary Examiner* — Yong Chu
*Assistant Examiner* — Sonya Wright
(74) *Attorney, Agent, or Firm* — Dentons US LLP

(57) ABSTRACT

Diesters are prepared by first hydrolyzing dinitrile compounds into imide compounds and then reacting such imide compounds with at least one alcohol.

17 Claims, No Drawings

PRODUCTION OF DIESTERS FROM DINITRILE COMPOUNDS

CROSS-REFERENCE TO EARLIER APPLICATIONS

This application national phase of PCT/EP 2008/064218, filed Oct. 21, 2008 and designating the United States (published in the French language on May 7, 2009 as WO 2009/056477 A1; the title and abstract were also published in English), which claims foreign priority under 35 U.S.C. §119 of FR 0707566 filed Oct. 31, 2007, each hereby expressly incorporated by reference in its entirety and each assigned to the assignee hereof.

The present invention relates to a process for the manufacture of diesters starting from dinitrile compounds.

It relates more particularly to a process for the manufacture of diester compounds starting from dinitrile compounds employing a hydrolysis of dinitrile compounds.

It relates more particularly still to a process for the manufacture of diesters starting from branched dinitrile compounds, such as methylglutaronitrile or branched dinitrile compounds obtained as by-products in the process for the manufacture of adiponitrile by hydrocyanation of butadiene.

Oxygen-comprising solvents based on diesters are increasingly used as replacements for other hydrocarbon, chlorinated or oxygen-comprising solvents which are more aggressive toward the environment.

Specifically, diester solvents, such as those sold under the known name of Rhodiasolv® RDPE obtained from a mixture of adipic acid, glutaric acid and succinic acid, exhibit the advantage of having a very favorable toxicological profile and are biodegradable and easy to recycle. Diester compounds obtained from branched compounds and more particularly from a mixture of methylglutaronitrile, ethylsuccinonitrile and adiponitrile have also been proposed in patent application WO2007/101929.

In this patent application, a manufacturing process has been described which consists in reacting the dinitrile compounds with an alcohol in the presence of an inorganic acid, followed by a hydrolysis. This process is known under the name of the Pinner reaction. However, an ammonium salt is obtained as by-product in this process.

One of the aims of the present invention is to provide a process for the manufacture of diesters starting from dinitrile compounds which does not exhibit the disadvantages of the processes of the prior art and which in particular does not generate significant effluence or by-products possibly harmful to the environment.

To this end, a subject matter of the invention is a process for the manufacture of at least one diester compound comprising the following stages:
a) preparation of at least one imide compound of the following general formula (I):

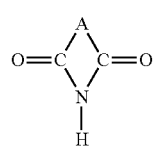
(I)

where A represents a linear or branched divalent hydrocarbon radical comprising from 2 to 12 carbon atoms, by hydrolysis in the presence of water of at least one dinitrile compound of following general formula (III):

b) then reaction between the imide compound and at least one alcohol of following general formula (II):

where R represents a linear or branched aliphatic, cycloaliphatic, aromatic or arylalkyl hydrocarbon radical comprising from 1 to 20 carbon atoms which can comprise heteroatoms, so as to obtain a reaction product comprising at least one diester compound of following general formula (IV) and optionally by-products of different formula (e):

characterized in that:
  at least one of the stages is carried out in the presence of a catalyst, and
  if both stages are carried out in the presence of a catalyst, then stage b) is carried out in the presence of at least one catalyst other than that employed during stage a).

The invention also relates to the products, thus material compositions, capable of being obtained, or obtained directly, by this process. The invention also relates to the use of these products or material compositions, in particular as solvents, cosolvents, crystallization inhibitors, cleaning and/or degreasing agents, or stripping agents.

DEFINITIONS

In the description, "catalyst" denotes the catalyst material in its native form or as a mixture with a matrix or a support prepared according to techniques known to a person skilled in the art.

Acid catalyst is understood to mean an acid catalyst within the Lewis meaning, as defined in the literature, in particular by Jerry March, Advanced Organic Chemistry, $3^{rd}$ edition, John Wiley and Sons, 1985, pp. 227 et seq., or a catalyst identified as such in the present patent application.

Basic catalyst is understood to mean a basic catalyst within the Lewis meaning, as defined in the literature, in particular by Jerry March, Advanced Organic Chemistry, $3^{rd}$ edition, John Wiley and Sons, 1985, pp. 227 et seq., or a catalyst identified as such in the present patent application.

Substantially without catalyst is understood to mean:
  that a fixed bed of catalyst is not employed, and
  that catalysts other than a fixed bed are not employed in amounts by weight, excluding the support, if present, with respect to the reactants, of greater than 1%, preferably than 0.5%, preferably than 0.1%, preferably 0.01%.

In the present patent application, a material composition denotes a mixture of several compounds, for example a reaction compound comprising several compounds. It can in particular concern products resulting from reactants as mixtures, exhibiting the same type of reactive functional groups. A material composition preferably comprises at least 50% by weight of compounds corresponding to the same chemical formula (exact formula, or general formula, or average formula), preferably at least 75%, preferably at least 90%, preferably at least 99%.

Stage a) can be regarded as a stage of cyclizing hydrolysis. In the present patent application, stage a) is also referred to as "cyclizing hydrolysis".

Operating Conditions

Stage a) and/or stage b) can be carried out in the vapor phase. Stage b) can be carried out in the liquid phase or in the vapor phase. According to one embodiment, both stages are carried out in the vapor phase. According to another embodiment, stage a) is carried out in the vapor phase and stage b) is carried out in the liquid phase. For the stages carried out in the vapor phase, the reaction medium can be brought into contact with the catalyst after having been vaporized.

Stage a) is preferably carried out in the vapor phase in the presence of a solid catalyst.

According to a specific embodiment:
  stage a) is carried out in the presence of a solid acid catalyst, and
  stage b) is carried out in the presence of a basic catalyst.

According to another specific embodiment:
  stage a) is carried out in the presence of a solid acid catalyst, and
  stage b) is carried out substantially without catalyst.

These two forms make it possible in particular to obtain high conversion and/or high selectivity and/or to limit undesirable by-products, which cannot, for example, be reintroduced into the preparation process after an easy conversion.

Acid or basic catalysts of use are mentioned below.

Stage a) is advantageously carried out at a temperature of less than 500° C., preferably of between 250° C. and 450° C. Furthermore, the molar ratio of the water to the nitrile compound is advantageously between 2 and 20 and preferably between 4 and 8.

Stage b) is advantageously carried out with a molar ratio of the alcohol to the imide compound of between 1 and 30 and preferably of between 5 and 20. For this stage, it is preferable to use a large excess of alcohol and optionally to subsequently reuse the unreacted excess. This makes it possible in particular to increase the selectivity.

Stage b) is advantageously carried out in the liquid phase at a temperature of less than 400° C. and preferably between 100 and 300° C., for example between 150° C. and 250° C., preferably at a pressure of 1 to 100 bar, in particular of 10 to 100 bar, for example between 15 and 25 bar, or between 30 and 50 bar, preferably autogenous pressure. According to a preferred embodiment, stage b) is carried out in the liquid phase, the alcohol being used both as reactant and as solvent medium, in excess.

It is mentioned that, during stage b), ammonia is formed. It can be removed during this stage, for example by withdrawing it from the reactor in the gaseous form (in a gaseous head space of the reactor, if stage b) is carried out in the liquid phase). It can in particular be withdrawn using an appropriate device, for example which makes it possible to keep the pressure constant, for example which allows the gas to escape when the pressure exceeds a certain value, and which makes possible, if appropriate, liquefaction after escaping. This device can be separated from the reactor by a pipe. The removal of the ammonia makes it possible in particular to promote the reaction and to limit the formation of by-products. The removal of ammonia can be accompanied by simultaneous removal of alcohol, also in the gaseous form. Preferably, an attempt is made to limit the simultaneous removal of alcohol. It is possible, for example, to this end, to cool the gases along a pipe separating the reactor and device, so as to liquefy at least a portion of the alcohol and to return it to the reactor. The gas(es) removed can be recovered and reused, if appropriate after separation of the ammonia and the alcohol. After separation, the alcohol can be reused in carrying out stage b).

Stage a) and stage b) can be carried out continuously or batchwise, in types of reactor which optionally make it possible to use a solid catalyst, either in the form of a fixed bed or of a fluidized bed. The reaction can be carried out at atmospheric pressure or under a higher pressure, for example under a pressure which can range up to 100 bar, preferably up to 30 bar. The pressure can be the autogenous pressure of the reaction medium at the temperature at which the stages are carried out.

The diester compound, after condensation, is extracted from the reaction medium by the usual techniques for the separation and purification of organic compounds, such as distillation or liquid/liquid extraction, for example.

It is noted that the imide compound obtained by hydrolysis of the dinitrile compound can advantageously be separated from the reaction medium and purified by the usual techniques. However, it is also possible to use the reaction medium obtained after the hydrolysis stage, without separation or purification, directly as reactant in the stage of reaction with an alcohol.

It is noted in particular that the process can comprise the following stage c), after stage b):
stage c): heating the reaction product from stage b) and distillation, so as to recover the diester compound.

Stage b), when it is carried out substantially without catalyst or in the presence of a basic catalyst, can result in by-products which it is possible to easily reconvert to imide, in particular by heating, for example during a distillation. It has been found that the use of an acid catalyst during this stage can promote the formation of undesirable by-products which cannot easily be converted. Thus, the reaction product from stage b) can comprise, in particular when this stage is carried out substantially without catalyst or in the presence of a basic catalyst, a by-product which is advantageously converted to imide of formula (I) during stage c) and which is reused in carrying out stage b).

The dinitrile compound is preferably chosen from the group comprising methylglutaronitrile, ethylsuccino-nitrile, adiponitrile and mixtures thereof.

The alcohol is preferably chosen from the group comprising methanol, propanol, isopropanol, benzyl alcohol, ethanol, n-butanol, isobutanol, pentanols, cyclohexanol, hexanol, isooctanol, 2-ethylhexanol and mixtures thereof. It is possible to employ mixtures of alcohols, such as fusel oil.

Acid Catalysts

The acid catalyst is preferably a solid catalyst. It can in particular be a solid acid catalyst, typically used in the heterogeneous phase, for example chosen from:
  metal oxides, such as alumina, titanium oxides, silica/alumina mixtures and the like,
  zeolites in the acid form,
  clays in the acid form,
  acid phosphates, such as $NaH_2PO_4$, or silicon pyrophosphate.

The acid catalysts can be provided in various forms in the process of the invention: powder, beads, crushed materials, extrudates in the form of hollow or solid cylindrical granules or of a honeycomb, or pellets, it being possible for the shaping optionally to be carried out using a product binder. These forms can be obtained in particular by extrusion, molding, compacting or any other type of known process. In practice, at the industrial level, it is the granule, bead or extruded forms which are most advantageous, both with regard to efficiency and with regard to convenience of use.

"Zeolite" is understood to mean a crystalline tectosilicate of natural or synthetic origin, the crystals of which result from the three-dimensional assembly of tetrahedral $SiO_4$ and $TO_4$ units, T being a trivalent element, such as aluminum, gallium, boron or iron, preferably aluminum. Zeolites of aluminosilicate type are the most common. Zeolites exhibit, within the crystal lattice, a system of cavities connected to one another by channels with a well defined diameter, which are known as pores. They can exhibit a one-dimensional, two-dimensional or three-dimensional network of channels. It is possible to employ a natural or synthetic zeolite.

Mention may be made, as examples of natural zeolites capable of being used, of, for example, chabazite, clinoptilolite, erionite, phillipsite and offretite.

Synthetic zeolites are also suitable. Mention may be made, by way of illustration of the latter, of those with a one-dimensional network, such as zeolite ZSM-4, zeolite L, zeolite ZSM-12, zeolite ZSM-22, zeolite ZSM-23 or zeolite ZSM-48. Mention may be made, as examples of zeolites with a two-dimensional network preferably employed, of mordenite or ferrierite. As regards the zeolites with a three-dimensional network, zeolite β, zeolite Y, zeolite X, zeolite ZSM-5, zeolite ZSM-11 or offretite may more particularly be named.

Use may in particular be made of zeolites which are in the following forms:

mazzite with an Si/Al atomic ratio of 3.4,
zeolite L with an Si/Al atomic ratio of 1.5 to 3.5,
mordenite with an Si/Al atomic ratio of 5 to 150, preferably of 10 to 100 and more preferably still of 10 to 50,
ferrierite with an Si/Al atomic ratio of 3 to 10,
offretite with an Si/Al atomic ratio of 4 to 8.5,
zeolites β with an Si/Al atomic ratio of 10 to 100, preferably 12 to 50,
zeolites Y, in particular the zeolites obtained after dealumination treatment (for example, hydrotreatment, washing with hydrochloric acid or treatment with $SiCl_4$), and mention may more particularly be made of zeolites US-Y with an Si/Al atomic ratio of greater than 3, preferably of between 6 and 60,
zeolite X of faujasite type with an Si/Al atomic ratio of 0.7 to 1.5,
zeolite ZSM-5 or aluminum silicalite with an Si/Al atomic ratio of 10 to 500,
zeolite ZSM-11 with an Si/Al atomic ratio of 5 to 30.

Among all these zeolites, recourse is preferably had, in the process of the invention, to zeolites US-Y.

The zeolite employed is in acid form. If necessary, a treatment is carried out which renders it acidic. To this end, recourse is had to conventional treatments. For the purposes of clarity, the acidic nature of the zeolites employed in the examples below is indicated by the prefix H.

Furthermore, it is possible to deactivate the external surface of the zeolites employed as catalyst. This type of treatment is well known to the person skilled in the art. It can in particular consist of a dealumination with steam or of an acid treatment or of a silylation.

The zeolites which can be employed are known products described in the literature [cf. Atlas of zeolites structure types by W. M. Meier and D. H. Olson published by the Structure Commission of the International Zeolite Association (1992)].

The zeolite constitutes the catalytic phase. It can be used alone or as a mixture with an inorganic matrix. In the specific case where the catalyst is used as a mixture with a matrix, this matrix can be chosen from metal oxides, such as aluminum, silicon and/or zirconium oxides, or from clays and more particularly kaolin, talc or montmorillonite. In such a catalyst, the content of active phase can represent from 5 to 100% of the weight of the catalyst.

According to a specific form of the invention, the zeolite used is a zeolite US-Y in acid form and with an Si/Al ratio of greater than 3 and preferably from 10 to 50.

The suitable clays which can be employed as acid catalyst can in particular be phyllosilicates, which are categorized by groups according to their nature and their physicochemical properties, among which groups may be mentioned kaolins, serpentines, smectites or montmorillonites, illites or micas, glauconites, chlorites or vermiculites, attapulgites or sepiolites, mixed-layer clays, allophanes or imogolites and high-alumina clays.

Some clays possess a lamellar structure with an expandable network. They exhibit the distinctive feature of adsorbing various solvents, in particular water, between the sheets of which they are composed, which brings about swelling of the solid as a result of the weakening of the electrostatic bonds between the sheets. These clays belong essentially to the smectites group (or also montmorillonite group) and, for some of them, to the vermiculites group.

Their structure is composed of "basic" sheets comprising three layers: two simple layers of $SiO_4$ tetrahedra in which a portion of the silicon can be replaced by other cations in the tetrahedral position, such as $Al^{3+}$ or optionally $Fe^{3+}$, and, between these two layers of tetrahedra, a layer of oxygen octahedra, at the center of which are situated metal cations, such as $Al^{3+}$, $Fe^{3+}$ or $Mg^{2+}$. This octahedral layer is composed of a compact stack of oxygens originating either from the vertices of the preceding tetrahedra or from hydroxyl groups OH. The compact hexagonal network of these oxygens comprises 6 octahedral cavities.

When the metal cations occupy 4 of these cavities (2 cavities out of 3, as in the case of aluminum, for example), the layer is said to be dioctahedral; when they occupy all the cavities (3 cavities out of 3, as in the case of magnesium, for example), the layer is said to be trioctahedral.

The basic sheets of these clays carry negative charges which are compensated for by the presence of exchangeable cations: alkali metal cations, such as $Li^+$, $Na^+$ or $K^+$, alkaline earth metal cations, such as $Mg^{2+}$ or $Ca^{2+}$, and optionally the hydronium ion $H_3O^+$. The smectites have charge densities on the sheets which are lower than those of the clays of the vermiculite type: approximately 0.66 charge per unit cell, against 1 to 1.4 charges per unit cell for the vermiculites.

The compensating cations are essentially sodium and calcium in the smectites and magnesium and calcium in the vermiculites. From the viewpoint of the charge densities, smectites and vermiculites are intermediates between talc and pyrophyllite, on the one hand, the sheets of which are neutral, and micas, on the other hand, characterized by a high charge density on the sheets (approximately 2 per unit cell) generally compensated for by $K^+$ ions.

The interlayer cations of the smectites and vermiculites can be fairly easily replaced by ion exchange by other cations, such as, for example, ammonium ions or alkaline earth metal ions or rare earth metal ions.

The swelling properties of clays depend on various factors, including the charge density and the nature of the compensating cation. Thus, smectites, the charge density of which is lower than that of vermiculites, exhibit swelling properties which are markedly superior to those of the latter and thus constitute a highly advantageous category of solids. The repeat distance or basal spacing represents the shortest distance separating two crystallographically identical units situated in two adjacent sheets. The basal spacing of smectites can thus reach, by swelling, values ranging from 1 nm approximately to more than 2 nm.

Mention may be made, among "swelling" phyllite-like silicates of the smectite type, of the following main solids of general formula:

$$(M_1^{n+})_{x/n}(M_2)_2^{VI}(M_3)_4^{IV}O_{10}(OH)_2$$

where $M_1$ is the interlayer cation
$M_2$ is the metal in the octahedral position
$M_3$ is the metal in the tetrahedral position
x is the number of charges contributed by the cation $M_1$
The dioctahedral smectites
  montmorillonite $(H,Na,Ca_{1/2})_x(Mg_xAl_{2-x})^{VI}Si_4^{IV}O_{10}(OH)_2$
  beidellite $(H,Na,Ca_{1/2})_xAl_2^{VI}(Al_xSi_{4-x})^{IV}O_{10}(OH)_2$
  nontrolite $(H,Na,Ca_{1/2} \ldots)_x(Fe,Al)_2^{VI}(Al_xSi_{4-x})^{IV}O_{10}(OH)_2$
The trioctahedral smectites
  hectorite $Na_x(Li_xMg_{3-x})^{VI}Si_4^{IV}O_{10}(OH)_2$
  saponite $Na_xMg_3^{VI}(Al_xSi_{4-x})^{IV}O_{10}(OH)_2$
  stevensite $Na_{2x}Mg_{3-x}^{VI}Si_4^{IV}O_{10}(OH)_2$ After adsorption in a smectite of water or of a polar organic solvent to saturation, the interlayer spacing (between two sheets) is at a maximum. It can reach a value in the vicinity of 1 nm.

These solids are thus potentially advantageous in catalysis as their potential specific surface and their potential acidity are high.

According to a specific form of the invention, the clay which constitutes the acid catalyst is a smectite. More preferably, the clay is montmorillonite.

Some clays unfortunately have the disadvantage of losing their expanded nature on heating to 100° C. and, for this reason, of not retaining the increase in specific surface resulting from their expansion. This is the case in particular with smectites. Various methods have been described in the prior art for introducing, between the sheets of smectites, pillars or bridges in order to obtain bridged smectites which retain a high interlayer spacing after having been subjected to a heat treatment.

One method, which consists in introducing bridges composed of oligomers of a hydroxide of a metal, in particular of aluminum hydroxide, has been described by Lahav, Shami and Shabtai in Clays and Clay Minerals, vol. 26 (No. 2), pp. 107-115 (1978), and in French patent 2 394 324. The formation of bridges composed of oligomers of mixed hydroxides of silicon and of boron is described in U.S. Pat. No. 4,248,739. A technique for bridging smectites by dialysis using hydroxides of aluminum, of chromium, of zirconium and titanium, and the like, is claimed in patent EP 0 073 718.

The principle of these methods consists in bringing the clay into contact with a solution comprising more or less oligomerized ionic entities of the hydroxy-aluminum type (in the case of aluminum). This operation is generally carried out in a solution of relatively low concentration, at a temperature of less than 80° C. and if possible in the absence of cloudiness formed by the beginning of precipitation of the metal hydroxide. The concentrations of the metal ion and of the clay have to be optimized in order for there to be sufficient formation of solid pillars and for the porosity of the clay not to be greatly reduced by the insertion of an excessively large amount of metal oxide.

When the interlayer alkali metal or alkaline earth metal ions are replaced by protons, either directly, using a very dilute solution, or, preferably, by exchange with an ammonium salt, followed by calcination between 300 and 700° C., the bridged smectites acquire a high acidity, although lower overall than those of conventional zeolites of Y or mordenite type, for example.

According to a specific alternative form of the invention, the catalyst can comprise, in addition to a clay, one or more other metal compounds, often referred to as doping agents, such as, for example, chromium, titanium, molybdenum, tungsten, iron or zinc compounds. Among these doping agents, chromium and/or iron and/or titanium compounds are regarded as the most advantageous. These doping agents usually represent, by weight per weight of clay, from 0% to 10% and preferably from 0% to 5%. The term "metal compound" is understood here to mean both the metal element and the metal ion or any combination comprising the metal element.

Another category of acid catalyst consists of a particulate catalyst obtained by shaping at least one simple or mixed inorganic oxide of at least one element chosen from the group consisting of silicon, aluminum, titanium, zirconium, vanadium, niobium, tantalum, tungsten, molybdenum or iron. These oxides can exist in an amorphous or crystalline form. Mention is made in particular of titanium dioxide, preferably in the anatase form. It can in particular comprise a support.

The particulate catalyst can exhibit a macroporosity characterized by a pore volume, corresponding to the pores with a diameter of greater than 500 Å, of greater than or equal to 5 ml/100 g. This macroporosity is advantageously formed during the process of shaping the particles by techniques described below or such as, for example, the addition of a pore-forming agent.

The catalyst may first of all be in the form of beads of inorganic oxides resulting from an oil drop shaping operation (or drop coagulation). Beads of this type can, for example, be prepared by a similar process to that described for the formation of alumina beads in patents EP-A-0 015 801 or EP-A-0 097 539. The porosity can be controlled in particular, according to the process described in patent EP-A-0 097 539, by drop coagulation of an aqueous suspension or dispersion of inorganic oxide. The beads can also be obtained by the process of agglomeration in a granulator or rotating drum.

The catalyst may also be in the form of extrudates of inorganic oxides. The latter can be obtained by kneading and then extruding a material based on the inorganic oxide. The porosity of these extrudates can be controlled by the choice of the oxide employed and by the conditions for preparing this oxide or by the conditions for kneading this oxide before extrusion. The inorganic oxide can thus be mixed, during the kneading, with pore-forming agents. By way of example, the extrudates can be prepared by the process described in U.S. Pat. No. 3,856,708.

Similarly, beads of controlled porosity can be obtained by addition of pore-forming agent and agglomeration in a rotating pan or granulator or by the oil drop process.

According to a specific embodiment, the catalyst particles exhibit a specific surface of greater than 10 m²/g and a pore volume of equal to or greater than 10 ml/100 g, the pore volume corresponding to the pores with a diameter of greater than 500 Å being greater than or equal to 10 ml/100 g.

According to another specific embodiment, the catalyst particles exhibit a specific surface of greater than 50 m²/g.

Advantageously, they exhibit a total pore volume of greater than or equal to 15 ml/100 g with a pore volume, corresponding to the pores with a diameter of greater than 200 Å, of greater than or equal to 15 ml/100 g, preferably of greater than or equal to 20 ml/100 g.

These particulate catalysts can also comprise at least one element chosen from the list consisting of silicon, titanium, zirconium, vanadium, niobium, tantalum, tungsten, molybdenum or iron or be obtained by deposition and/or adsorption on the support of at least one oxygen compound of at least one element chosen from the group consisting of the elements belonging to Groups 1 to 16 of the Periodic Table of the Elements (new Table). These elements or compounds are deposited, adsorbed or co-kneaded on or with the particulate catalyst.

In the procedure comprising a porous particulate catalyst supporting oxygen compounds of elements, these elements are advantageously chosen from the list comprising silicon, titanium, zirconium, vanadium, niobium, tantalum, tungsten, molybdenum, phosphorus, boron, iron, alkali metals, alkaline earth metals and rare earth metals. The oxygen compound is advantageously a simple or mixed oxide of one or more of the elements mentioned above.

In this embodiment, the porous catalyst is preferably an aluminum oxide. Advantageously, this alumina exhibits the specific surface and pore distribution characteristics defined above.

The concentration by weight of oxygen compound supported on a porous support is advantageously between 1000 ppm and 30%, expressed as weight of element of the oxygen compound with respect to the total weight of the catalyst. This concentration is more preferably between 0.5% and 15% by weight.

When the porous supports correspond to aluminas in accordance with the invention, the latter are generally obtained by dehydration of gibbsite, bayerite, nordstrandite or their various mixtures. The various processes for the preparation of the aluminas are described in the Kirk-Othmer encyclopaedia, volume 2, pages 291-297.

The aluminas employed in the present process can be prepared by bringing a hydrated alumina, in the finely divided form, into contact with a stream of hot gas at a temperature of between 400° C. and 1000° C., then maintaining contact between the hydrate and the gases for a period of time ranging from a fraction of a second up to 10 seconds, and finally separating the partially dehydrated alumina and the hot gases. Reference may in particular be made to the process described in U.S. Pat. No. 2,915,365.

It is also possible to autoclave agglomerates of aluminas obtained above, in aqueous medium, optionally in the presence of acid, at a temperature of greater than 100° C. and preferably of between 150° C. and 250° C., for a period of time preferably of between 1 and 20 hours, and then to dry and calcine them.

The calcination temperature is adjusted so that specific surfaces and pore volumes lying within the regions of values indicated above are obtained.

In a specific embodiment, use is made of a catalyst, a porous particulate catalyst based on titanium dioxide, preferably in the anatase form, optionally supporting an oxygen compound chosen from the list consisting of silicon, aluminum, zirconium, vanadium, niobium, tantalum, tungsten, molybdenum or iron or be obtained by deposition and/or adsorption on the support of at least one oxygen compound of at least one element chosen from the group consisting of the elements belonging to Groups 1 to 16 of the Periodic Table of the Elements (new Table). These elements or compounds are deposited, adsorbed or co-kneaded on or with the particulate catalyst. The content of titanium dioxide can, for example, be from 10 to 80% by weight, the remainder being, for example, silica or alumina.

The catalysts of the invention advantageously have a specific surface of greater than 50 m$^2$/g.

In addition, they advantageously exhibit pores with a diameter of greater than 0.1 μm, the pore volume contributed by these pores being greater than or equal to 5 ml/100 g, advantageously greater than or equal to 10 ml/100 g.

In a preferred embodiment of the invention, these catalysts also comprise pores with a diameter of equal to or greater than 0.5 μm, the corresponding pore volume being equal to or greater than 5 ml/100 g, preferably greater than or equal to 10 ml/100 g.

This pore volume generated by the pores with a diameter of greater than 500 Å, preferably of greater than 0.1 μm and advantageously of greater than 0.5 μm makes it possible to obtain catalysts with a high cycle time.

According to the invention, the catalysts comprising oxygen compounds supported by a porous catalyst are obtained generally by impregnation of the catalyst, in particular of alumina, by a solution of a salt or compounds of the elements mentioned above and are then dried and calcined at a temperature equal to or greater than 400° C. in order to convert, optionally and advantageously, said compounds or salts to oxygen compounds, preferably to oxides. The oxides are deposited at the surface of the pores of the porous catalyst.

In another embodiment, the compounds of elements can be added to the material constituting the porous catalyst before it is shaped or during the shaping process.

The impregnated catalysts are preferably calcined under an oxidizing atmosphere, such as air.

Use may in particular be made, as acid catalyst, of an acid phosphate, generally a metal phosphate, of general formula:

$$(PO_4)_n H_h M, (Imp)_p$$

in which:
M represents a divalent, trivalent, tetravalent or pentavalent element chosen from Groups 2a, 3b, 4b, 5b, 6b, 7b, 8, 2b, 3a, 4a and 5a of the Periodic Table of the Elements or a mixture of several of these elements or M=O, Imp represents a basic impregnation compound composed of an alkali metal or alkaline earth metal or of mixtures of several of these metals, in combination with a counteranion in order to provide electrical neutrality, n represents 1, 2 or 3, h represents 0, 1 or 2, p represents a number between 0 and ⅓ and corresponds to a molar ratio of the impregnating material Imp to the impregnated material $(PO_4)_n H_h M$.

Mention may in particular be made, among the metals of Groups 2a, 3b, 4b, 5b, 6b, 7b, 8, 2b, 3a, 4a and 5a of the Periodic Table of the Elements, of beryllium, magnesium, calcium, strontium, barium, aluminum, boron, gallium, indium, yttrium, the lanthanides, such as lanthanum, cerium, praseodymium, neodymium, samarium, europium, gadolinium, terbium, dysprosium, holmium, erbium, thulium, ytterbium and lutetium, zirconium, titanium, vanadium, niobium, iron, germanium, tin or bismuth.

Among the phosphates of lanthanides, it is possible to distinguish a first family which brings together orthophosphates of light rare earth metals, also known as ceric rare earth metals, including lanthanum, cerium, praseodymium, neodymium, samarium and europium. These orthophosphates are dimorphic. They exhibit a hexagonal structure and change towards a monoclinic structure when they are heated at a temperature of 600 to 800° C.

A second family of phosphates of lanthanides brings together the orthophosphates of gadolinium, of terbium and of dysprosium. These orthophosphates exhibit the same structure as the orthophosphates of ceric rare earth metals but additionally exhibit a third crystalline phase of quadratic structure at high temperature (approximately 1700° C.)

A third family of phosphates of lanthanides brings together the orthophosphates of heavy rare earth metals, also known as yttric rare earth metals, including yttrium, holmium, erbium, thulium, ytterbium and lutetium. These compounds crystallize solely in the quadratic form.

Recourse is preferably had, among the various abovementioned families of orthophosphates of rare earth metals, to the orthophosphates of ceric rare earth metals.

Use may be made of metal phosphates of the above formula which are mixtures of phosphates of several of the metals indicated above or mixed phosphates of several of the metals indicated above or also mixed phosphates comprising one or more of the metals indicated above and one or more other metals, such as alkali metals or alkaline earth metals.

The counteranions participating in the formula of the impregnation compound Imp are basic. Use may in particular be made of the hydroxide, phosphate, hydrogenphosphate, dihydrogenphosphate, chloride, fluoride, nitrate, benzoate or oxalate ions, without this list being limiting.

The molar ratio p is preferably between 0.02 and 0.2.

If reference is made to the general techniques for the preparation of phosphates (such as described in particular in Pascal P. "Nouveau traité de chimie minérale" [New Treatise on Inorganic Chemistry], volume X (1956), pages 821-823, and in Gmelins "Handbuch der anorganischen Chemie" [Handbook of Inorganic Chemistry] (8th edition), volume 16 (C), pages 202-206 (1965)), it is possible to distinguish two main routes of access to phosphates. On the one hand, the precipitation of a soluble salt of the metal (chloride, nitrate) by ammonium hydrogenphosphate or phosphoric acid. On the other hand, the dissolution of the oxide or of the carbonate of the metal (which are insoluble) with phosphoric acid, generally under warm conditions, followed by precipitation.

The precipitated phosphates obtained according to one of the routes indicated can be dried, treated with an organic base (such as ammonia) or an inorganic base (such as an alkali metal hydroxide) and be subjected to a calcination, it being possible for these three operations to be carried out in the order shown or in a different order.

The metal phosphates of the above formula for which the symbol p is greater than 0 can be prepared by impregnation of the compound $(PO_4)_nH_hM$, prepared according to one of the techniques described above, with a solution or a suspension of Imp in a volatile solvent, such as water, preferably.

The results improve as Imp increases in solubility and the more recently the compound $(PO_4)_nH_hM$ has been manufactured.

Thus, an advantageous process for the preparation of these phosphates consists:
 a) in synthesizing the compound $(PO_4)_nH_hM$ and then, preferably without separating $(PO_4)_nH_hM$ from the reaction medium,
 b) in introducing the impregnating material Imp into the reaction medium;
 c) in separating the possible residual liquid from the reaction solid;
 d) in drying and optionally in calcining.

The performances of these catalysts and in particular their resistance to deactivation can be further improved by calcination. The calcination temperature will advantageously be between 300° C. and 1000° C. and preferably between 400° C. and 900° C. The duration of the calcination may vary within wide limits. By way of indication, it generally lies between 1 hour and 24 hours.

Mention may more particularly be made, among the catalysts which can be used, of lanthanum phosphate, calcined lanthanum phosphate, lanthanum phosphate in combination with a cesium, rubidium or potassium derivative, calcined cerium phosphate, cerium phosphate in combination with a cesium, rubidium or potassium compound, samarium phosphate in combination with a cesium, rubidium or potassium compound, aluminum phosphate, aluminum phosphate in combination with a cesium, rubidium or potassium compound, calcined niobium phosphate, niobium phosphate in combination with a cesium, rubidium or potassium compound, calcined zirconium hydrogenphosphate or zirconium hydrogenphosphate in combination with a cesium, rubidium or potassium compound.

The orthophosphates described above can be used as a mixture with phosphoric acid ($H_3PO_4$).

Use may also be made, as catalyst, of pyrophosphates of rare earth metals, in particular of lanthanum, alone or as a mixture with the orthophosphates described above. Such catalysts are described in European patent EP 1 066 255.

Basic Catalysts

The basic catalyst may or may not be solid. It can be employed in a heterogeneous or nonheterogeneous form, in particular during stage b). It can in particular be employed in the form dissolved in the reaction medium, in particular during stage b).

According to a first embodiment, use may be made, as basic catalyst, of an organic salt comprising a basic anion. Alkali metal or alkaline earth metal salts of compounds comprising a sulfate, sulfonate, phosphate or phosphonate group or of organic compounds comprising a carboxylate or alkoxide (or "alkylate") group are suitable in particular. Mention is made in particular of potassium, sodium or lithium alkoxides, in particular sodium ethoxide or lithium ethoxide.

According to a second embodiment, use may be made, as basic catalyst, of an inorganic base. It can be a nitrogenous or nonnitrogenous inorganic base.

Inorganic bases other than nitrogenous bases have the advantage of being of lower cost and of being less harmful environmentally. Finally, protection is achieved from any side reaction which may be observed with primary or secondary amines, for example.

Water-soluble alkali metal salts of hydroxide, inorganic carbonate or inorganic phosphate type are suitable in particular. Mention may in particular be made, by way of illustration of these bases, of hydroxides, such as NaOH, KOH or LiOH, and salts of strong bases with a weak acid, such as $K_2CO_3$ and $Na_2CO_3$, $K_3PO_4$ or $Li_3PO_4$.

According to a third embodiment, use may be made, as basic catalyst, of a solid heterogeneous basic catalyst. In this specific case, the base used can be a heterogeneous catalyst based on hydroxides and/or oxides of alkali metals, alkaline earth metals and/or lanthanides. It can in particular be magnesia (MgO), $Mg(OH)_2$, CaO, $Ca(OH)_2$, BaO, $Ba(OH)_2$.

It can in particular be a catalyst chosen from oxides, hydroxides and basic salts of alkaline earth metals and/or rare earth metals not exhibiting a degree of valency IV and from the minerals comprising them.

Use may in particular be made of the natural minerals or synthetic analogs which are composed of intercalated layers based on metal oxides or hydroxides, such as hydrotalcite. The catalyst can in particular be a natural hydrotalcite or a synthetic analog. These basic salts can comprise various combinations of metal cations $M^{2+}$, such as $Mg^{2+}$, $Zn^{2+}$, $Cu^{2+}$, $Ni^{2+}$, $Te^{2+}$ or $Co^{2+}$, and of the trivalent cations of $M^{3+}$ type, such as $Al^{3+}$, $Cr^{3+}$ or $Fe^{3+}$. The anions associated with these metal cations can be halogens, organic anions or also oxyanions. Mention may in particular be made, by way of representation of these hydrotalcites, of that corresponding to the formula $[Mg_6Al_2(O_4)_{16}]CO_3.4H_2O$.

Use may in particular be made of oxides and carbonates of rare earth metals, such as ytterbium and lanthanum.

According to a fourth embodiment, use is made of an alkali metal in the metallic form, for example sodium.

Mention is made, as examples of basic catalysts of particular use, of:
- alkali metal alkoxides (or "alkylates"), in particular sodium methoxide, sodium ethoxide, sodium tert-butoxide, potassium methoxide, potassium ethoxide or potassium tert-butoxide,
- metallic sodium,
- lanthanum oxide, or
- magnesium oxide.

Subsequent Reactions

It is noted that it is possible to prepare methyl diesters by using methanol as alcohol and then to carry out a transesterification with a heavier alcohol, such as propanol, isopropanol, benzyl alcohol, ethanol, n-butanol, isobutanol, pentanols, cyclohexanol, hexanol, isooctanol, 2-ethylhexanol and mixtures thereof, in order to obtain a heavier diester.

Other details or advantages of the invention may become apparent in the light of the examples which follow, without a limiting nature.

EXAMPLES

Example 1

Stage a)

Use is made, as starting material, of a mixture of dinitrile compounds with the following composition by weight:
- 86% by weight of methylglutaronitrile
- 11% by weight of ethylsuccinonitrile
- 3% by weight of adiponitrile.

1 ml/h of mixture of dinitriles and 1 ml/h of water are coinjected, using 2 syringe drivers, over a catalytic fixed bed composed of 4 ml of titanium oxide (anatase) placed between 2 layers of 5 ml of glass powder which is heated at 275° C. and swept with a nitrogen stream of 3 l/h. At the outlet of the reactor, the gases are condensed in a receiver placed in an ice bath. After reacting for 6 h, the products obtained are analyzed by gas chromatography. A yield of a mixture of imides of 94% is then obtained, for a conversion of the dinitriles of 97%.

Example 2.1

Stage b) with MgO 20 g of a mixture of imides (product from example 1), 175 g of methanol and 1 g of MgO (Prolabo) are introduced into a 300 ml stainless steel reactor. The reaction mixture is heated under autogenous pressure to 250° C. and these conditions are maintained for 6 h. After cooling and filtering off the catalyst, the reaction medium is analyzed by GC. A yield of diesters of 67% is obtained, for a conversion of imides of 90%.

Example 2.2

Stage b) with Lanthanum Oxide 20 g of a mixture of imides (product from example 1), 175 g of methanol and 1 g of $La_2O_3$ (Rhodia) are introduced into a 300 ml stainless steel reactor. The reaction mixture is heated under autogenous pressure to 250° C. and these conditions are maintained for 6 h. After cooling and filtering off the catalyst, the reaction medium is analyzed by GC. A yield of diesters of 62% is obtained, for a conversion of imides of 95%.

Example 2.3

Stage b) with Sodium Methoxide 20 g of a mixture of imides (product from example 1), 175 g of methanol and 0.5 g of sodium methoxide are introduced into a 300 ml stainless steel reactor. The reaction mixture is heated under autogenous pressure to 250° C. and these conditions are maintained for 6 h. After cooling, the reaction medium is analyzed by GC. A yield of diesters of 65% is obtained, for a conversion of imides of 92%.

Example 2.4

Stage b) with Potassium Tert-Butoxide 20 g of a mixture of imides (product from example 1), 175 g of methanol and 0.5 g of potassium tert-butoxide (Aldrich) are introduced into a 300 ml stainless steel reactor. The reaction mixture is heated under autogenous pressure to 250° C. and these conditions are maintained for 6 h. After cooling and filtering off the catalyst, the reaction medium is analyzed by GC. A yield of diesters of 67% is obtained, for a conversion of imides of 89%.

Example 2.5

Stage b) without Catalyst 20 g of a mixture of imides (product from example 1) and 175 g of methanol are introduced into a 300 ml stainless steel reactor. The reaction mixture is heated under autogenous pressure to 250° C. and these conditions are maintained for 6 h. After cooling, the reaction medium is analyzed by GC. A yield of diesters of 65% is obtained, for a conversion of imides of 85%.

Example 3.1

Example with Fusel Oil—Stage b) with Sodium Ethoxide 25 g of a mixture of imides (product from example 1) are introduced into a 300 ml pressure-resistant stainless steel reactor equipped with a device for continuously purging with ammonia, and 50 g of fusel oil from Wako (boiling point 110-130° C., density 0.810-0.850) and 5% w/w sodium ethoxide, with respect to the sum of the imides, are added. The reactor is closed and the reaction medium is heated to 250° C. with stirring. After reacting for 4 hours, the conversion of the imides is complete and a yield of diesters of 90% is obtained. The reaction medium is filtered, in order to recover the catalyst, and the filtrate is distilled, in order to separate the excess fusel oil and the mixture of diesters. The mixture of diesters distils in the 160-200° C. range under 20 mmHg.

Example 3.2

Example with Fusel Oil—Stage b) with Sodium Metal

The reaction is carried out as in example 4 using 2.5% w/w of sodium metal instead of the sodium ethoxide. A conversion of 100% and a yield of diesters of 91% are then obtained.

What is claimed is:

1. A process for the preparation of at least one diester compound comprising the following stages:
   a) preparing an imide compound of the following formula (I):

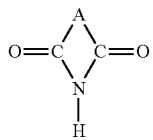

wherein A is a linear or branched divalent hydrocarbon radical having from 2 to 12 carbon atoms,
   by hydrolyzing, in the presence of water, at least one dinitrile compound of following formula (III):

NC-A-CN  (III)

and
   b) reacting said imide compound with at least one alcohol of the following formula (II):

R—OH  (II)

wherein R is a linear or branched aliphatic, cycloaliphatic, aromatic or arylalkyl hydrocarbon radical having from 1 to 20 carbon atoms and optionally containing heteroatoms,
   to obtain a reaction product comprising at least one diester compound of the following formula (IV) and optionally by-products of different formula(e):

R—OOC-A-COO—R  (IV)

wherein:
   stage a) is carried out in the vapor phase in the presence of a solid catalyst, and
   stage b) is carried out in the presence of at least one catalyst other than that employed during stage a).

2. The process as defined by claim 1, wherein stage b) is carried out in the presence of a basic catalyst, and said basic catalyst is selected from the group consisting of:
   organic salts comprising a basic anion,
   inorganic bases,
   heterogeneous basic catalysts, and
   alkali metals in the metallic form.

3. The process as defined by claim 1, wherein stage b) is carried out in the presence of a basic catalyst which comprises:
   an alkali metal alkoxide,
   metallic sodium,
   lanthanum oxide, or
   magnesium oxide.

4. The process as defined by claim 1, wherein stage a) is carried out in the presence of a solid acid catalyst, and stage b) is carried out in the presence of a basic catalyst.

5. The process as defined by claim 1, wherein stage b) is carried out in the liquid or vapor phase.

6. The process as defined by claim 1, wherein stage a) is carried out at a temperature of less than 500° C.

7. The process as defined by claim 1, wherein, during stage a), the molar ratio of the water to the nitrile compound ranges from 2 to 20.

8. The process as defined by claim 1, wherein, during stage b), the molar ratio of the alcohol to the imide compound ranges from 1 to 30.

9. The process as defined by claim 1, wherein the at least one dinitrile compound is selected from the group consisting of methylglutaronitrile, ethylsuccinonitrile, adiponitrile and mixtures thereof.

10. The process as defined by claim 1, wherein the at least one alcohol is selected from the group consisting of methanol, propanol, isopropanol, benzyl alcohol, ethanol, n-butanol, isobutanol, pentanols, cyclohexanol, hexanol, isooctanol, 2-ethylhexanol and mixtures thereof.

11. The process as defined by claim 1, wherein stage a) is carried out in the presence of a solid acid catalyst, and the solid acid catalyst is selected from the group consisting of:
    metal oxides, alumina, titanium oxides, silica/alumina mixtures,
    zeolites in the acid form,
    clays in the acid form,
    acid phosphates, $NaH_2PO_4$, and silicon pyrophosphate.

12. The process as defined by claim 11, wherein the solid acid catalyst comprises anatase titanium dioxide.

13. The process as defined by claim 1, wherein stage b) is carried out in the liquid phase at a temperature of less than 400° C., and at a pressure of 1 to 100 bar.

14. The process as defined by claim 1, further comprising a stage c), after stage b):
    stage c): heating the reaction product from stage b) and distilling, and recovering the diester compound.

15. The process as defined by claim 14, wherein the reaction product from stage b) comprises a by-product which is converted to an imide of formula (I) during stage c) and which is then employed in carrying out stage b).

16. The process as defined by claim 1, wherein, during stage b), ammonia is formed and then removed during this stage.

17. The process as defined by claim 1, wherein, in stage a) hydrolyzing, in the presence of water, at least one dinitrile compound precedes addition of the solid catalyst and wherein, in stage b), reacting said imide compound with at least one alcohol precedes addition of a catalyst other than the one used for stage a).

* * * * *